United States Patent
Sargent et al.

(10) Patent No.: US 11,183,294 B2
(45) Date of Patent: Nov. 23, 2021

(54) AUTOMATIC DETECTION AND REPLACEMENT OF IDENTIFYING INFORMATION IN IMAGES USING MACHINE LEARNING

(71) Applicant: International Business Machines Corporation, Armonk, NY (US)

(72) Inventors: Dustin M. Sargent, San Diego, CA (US); Sun Young Park, San Diego, CA (US); Dale Seegmiller Maudlin, Solana Beach, CA (US)

(73) Assignee: International Business Machines Corporation, Armonk, NY (US)

( * ) Notice: Subject to any disclaimer, the term of this patent is extended or adjusted under 35 U.S.C. 154(b) by 111 days.

(21) Appl. No.: 16/556,865

(22) Filed: Aug. 30, 2019

(65) Prior Publication Data

US 2021/0065881 A1   Mar. 4, 2021

(51) Int. Cl.
  *G16H 30/40*   (2018.01)
  *G06T 11/60*   (2006.01)
  (Continued)

(52) U.S. Cl.
  CPC ........... *G16H 30/40* (2018.01); *G06N 3/0454* (2013.01); *G06N 3/08* (2013.01); *G06N 20/20* (2019.01);
  (Continued)

(58) Field of Classification Search
  CPC ........... G16H 30/40; G06T 7/11; G06T 7/174; G06T 7/155; G06T 11/60;
  (Continued)

(56) References Cited

U.S. PATENT DOCUMENTS 6,067,399 A   5/2000   Berger
8,811,951 B1   8/2014   Faaborg et al.
(Continued)

FOREIGN PATENT DOCUMENTS

CN   1484114 A   3/2004

OTHER PUBLICATIONS

Tagare, Hemant D., C. Carl Jaffe, and James Duncan. "Medical image databases: A content-based retrieval approach." Journal of the American Medical Informatics Association 4.3 (1997): 184-198. (Year: 1997).*

(Continued)

*Primary Examiner* — Pinalben Patel
(74) *Attorney, Agent, or Firm* — John Noh; Edell, Shapiro & Finnan, LLC

(57) ABSTRACT

Methods and systems are provided for managing identifying information for an entity. The identifying information of the entity embedded in or associated with a digital image is detected, wherein the identifying information is selected from the group consisting of: text information and image information corresponding to one or more features of an entity. The text information may be removed from the digital image. The image information may be replaced with one or more computer generated synthetic images, wherein the computer generated synthetic images are based on a natural appearance of the digital image. The synthetic content, which may be generated by a GAN, is based on a natural appearance of the image. The medical image may also contain PHI in text-based fields associated with private tags/fields, which are automatically identified and removed using the systems and methods provided herein.

20 Claims, 7 Drawing Sheets

(51) Int. Cl.
| | |
|---|---|
| *G06T 7/11* | (2017.01) |
| *G06T 7/155* | (2017.01) |
| *G06N 3/08* | (2006.01) |
| *G06N 3/04* | (2006.01) |
| *G06N 20/20* | (2019.01) |
| *G06T 7/174* | (2017.01) |

(52) U.S. Cl.
CPC .............. *G06T 7/11* (2017.01); *G06T 7/155* (2017.01); *G06T 7/174* (2017.01); *G06T 11/60* (2013.01); *G06T 2207/20036* (2013.01)

(58) Field of Classification Search
CPC ............ G06T 2207/20036; G06N 3/08; G06N 20/20; G06N 3/0454
See application file for complete search history.

(56) References Cited

U.S. PATENT DOCUMENTS

| | | | |
|---|---|---|---|
| 10,205,708 B1 | 2/2019 | Fletcher et al. | |
| 2004/0027594 A1 | 2/2004 | Suzuki et al. | |
| 2007/0077550 A1 | 4/2007 | Tohma et al. | |
| 2008/0077604 A1* | 3/2008 | Bharara | G16H 30/20 |
| 2011/0069885 A1* | 3/2011 | Malik | G06T 11/60 |
| | | | 382/176 |
| 2013/0124951 A1* | 5/2013 | Shechtman | G06K 9/00718 |
| | | | 715/201 |
| 2013/0238096 A1 | 9/2013 | Kotlus | |
| 2014/0344948 A1 | 11/2014 | Hayato et al. | |
| 2015/0106194 A1 | 4/2015 | Holman et al. | |
| 2018/0008349 A1 | 1/2018 | Gillman | |
| 2018/0144465 A1* | 5/2018 | Hsieh | G06N 3/08 |
| 2018/0285592 A1 | 10/2018 | Sharifi et al. | |
| 2018/0349526 A1* | 12/2018 | Atsmon | G06T 17/05 |

OTHER PUBLICATIONS

International Search Report and Written Opinion in corresponding International Application No. PCT/IB2020/057830, dated Nov. 10, 2020, 8 pages.

Bhatia et al., A Mixed Based Classifier Approach for Sentiment Analysis, Thesis submitted for Master of Engineering in Software Engineering, Computer Science and Engineering Department, Thapar University, Patiala, Jun. 2015, 50 pages.

Lilien et al., Trading Privacy for Trust in Online Interactions, Idea Group, 2008, 35 pages.

Cao et al., Face Generation with Conditional Generative Adversarial Networks, 2017, 8 pages (available at https://www.semanticscholar.org/paper/Face-Generation-with-Conditional-Generative-Cao-Dulloor/b1ffd13e8f68401a603eea9806bc37e396a3c77d).

Moore et al., Safe (Compliant) De-Identification of Medical Images with Maximum Retention of Scientific Research Value, Cancer Imaging Archive, Washington University in St. Louis, School of Medicine, Presented at the Annual Meeting of the Radiological Society of North America (RSNA), 2012, 1 page.

\* cited by examiner

AUTOMATIC DETECTION AND REPLACEMENT OF IDENTIFYING INFORMATION IN IMAGES USING MACHINE LEARNING

BACKGROUND

1. Technical Field

Present invention embodiments relate to machine learning systems to identify and replace identifying information in images, and in particular, to automatic identification and replacement of protected health information in medical images with synthetic and/or generic data that comprises characteristics of the protected health information.

2. Discussion of the Related Art

Medical imaging studies may contain several forms of protected health information (PHI), which may be used to identify a specific person. This includes patient-specific information contained in the headers of medical image files, such as patient name and birthdate, or information contained in a medical report, such as patient address. Additionally, PHI may be found in private tags that are device or software specific.

PHI may also be found in the medical images themselves. For example, burned-in annotations in images may identify the patient. In some cases, the patient can be identified by anatomical features present in the medical imaging scan. For example, it may be possible to identify a person's face from a 3D rendering of a head CT scan, or by visualizing certain implants (e.g., dental, medical implants, etc.) or other unique features that may be visible in the images.

Present techniques to mitigate release of this information relies upon human intervention. Typically, a human reviewer manually reviews files to identify and replace text-based PHI. However, this approach is a time-consuming and error prone process. For example, human reviewers may miss information in private tags or in the images themselves. Additionally, identified data is often redacted or deleted, leading to data loss. Thus, current approaches are subject to accidental release of protected information, which may breach privacy laws and regulations by unknowingly or accidentally exposing personal health information.

SUMMARY

According to embodiments of the present invention, methods, systems, and computer readable media are provided for automatic removal of identifying information embedded in and/or associated with digital images. Removal of PHI may include replacing the PHI with content (e.g., generic and/or synthetic content) that does not contain PHI, to prevent identification of an entity associated with the digital image.

In some aspects, identifying information embedded in or associated with a digital image is detected, wherein the identifying information is selected from the group consisting of: text information and image information corresponding to one or more features (including anatomical features) associated with an entity. The text information may be removed from the digital image. The image information may be replaced with one or more computer generated synthetic images, wherein the computer generated synthetic images are based on a natural appearance of the digital image. The computer generated synthetic images may be generated by a machine learning system.

The image information may be replaced with one or more computer generated synthetic images, wherein the computer generated synthetic images are based on a natural appearance of the digital image (e.g., the synthetic images simulate real objects (e.g., anatomical features or other features) within the digital image to enable the digital image to appear to provide the real objects). For example, a synthetic image having a natural appearance may be an image in which an entity (e.g., a user, a machine learning system, etc.) is not able to distinguish whether the synthetic image is from a medical imaging study of a patient or is a computer generated image (e.g., generated by a machine learning system, etc.).

In embodiments, identifying information may be detected in a header file, in metadata or in other text-based representations associated with the digital image. This information may be detected and removed. In some aspects, removal may include replacing one or more types of identifying information with generic information comprising aspects of the identifying information, while preventing identification of the entity. PHI may be detected in private tags of header files. In other embodiments, the methods, systems and computer readable media provided herein may be configured to morph digital images containing medically relevant PHI to disguise patient identity.

It is to be understood that the Summary is not intended to identify key or essential features of embodiments of the present disclosure, nor is it intended to be used to limit the scope of the present disclosure. Other features of the present disclosure will become easily comprehensible through the description below.

BRIEF DESCRIPTION OF THE DRAWINGS

Generally, like reference numerals in the various figures are utilized to designate like components.

DETAILED DESCRIPTION

Methods, systems, and computer readable media are provided for automating removal of identifying or other information (e.g., protected health information (e.g., PHI, etc.)) for an entity in medical imaging or other studies. These techniques may minimize data loss by replacing patient-specific or identifying data with generic and/or synthetic data that contain aspects of the patient-specific data. These approaches replace image content and associated text, which may identify the patient, with generic content that retains characteristics of the PHI and/or synthetic images generated by the computer with a natural appearance, while removing sensitive PHI data.

Figure 1:
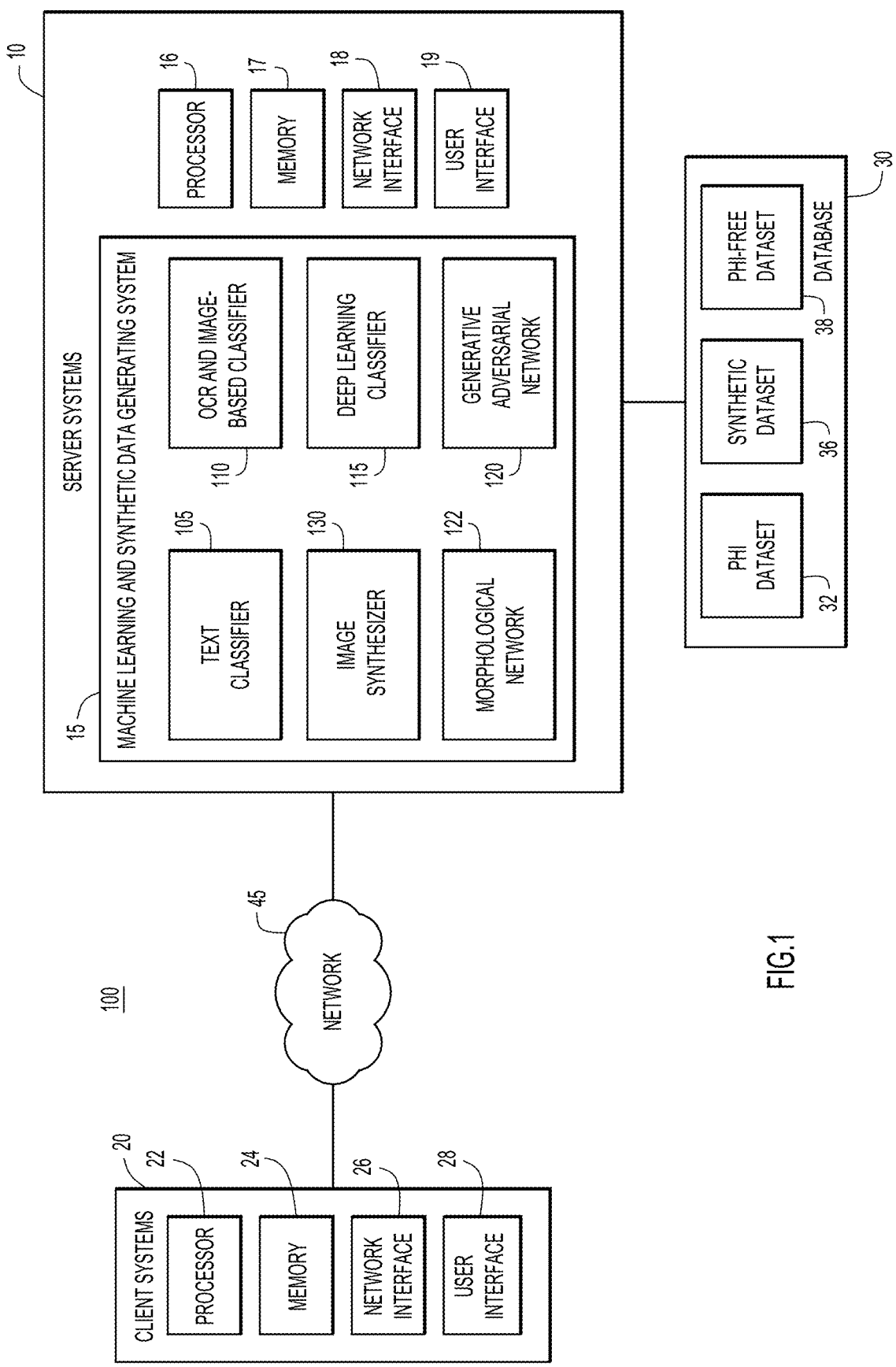
FIG. 1 is a diagrammatic illustration of an example computing environment for automatically identifying and mitigating PHI according to an embodiment of the present invention.

An example environment for use with present invention embodiments is illustrated in FIG. 1. Specifically, the environment includes one or more server systems 10, one or more client or end-user systems 20, a database 30, and network 45. Server systems 10 and client systems 20 may be remote from each other and may communicate over a network 45. The network may be implemented by any number of any suitable communications media, such as a wide area network (WAN), a local area network (LAN), Internet, Intranet, etc. Alternatively, server systems 10 and client systems 20 may be local to each other, and may communicate via any appropriate local communication medium, such as local area network (LAN), hardware, wireless link, Intranet, etc.

Client systems 20 enable users to submit datasets to server systems 10 for training a machine learning and synthetic data generating system and for using this system to identify and mitigate PHI from medical images. The server systems 10 include a machine learning and synthetic data generating system 15 comprising a text classifier 105, an OCR and image-based classifier 110, a deep learning classifier 115, a generative adversarial network 120, a morphological network 122, and an image synthesizer 130, as described herein. A database 30 may store various information for the analysis, such as a PHI dataset 32, a synthetic dataset 36, and a PHI-free dataset 38, etc. The PHI dataset 32 contains medical imaging files with patient specific information. The synthetic dataset 36 contains images generated by the generative adversarial network 120 or morphological network 122. The PHI-free dataset 38 contains images in which patient identifying information has been removed or modified.

The database system 30 may be implemented by any conventional or other database or storage unit, may be local to or remote from server systems 10 and client systems 20 and may communicate via any appropriate communication medium, such as local area network (LAN), wide area network (WAN), Internet, hardware, wireless link, Intranet, etc. The client systems may present a graphical user interface, such as a GUI, etc., or other interface, such as command line prompts, menu screens, etc., to solicit information from users pertaining to the desired datasets, identification and data mitigation, and may provide reports including analysis results of the dataset, including types, locations, and sources of PHI. In some aspects, the PHI-free dataset may be analyzed, e.g., by third parties, to correlate medical diagnostic information with characteristics of the PHI-free dataset. For example, PHI-free angiographic images may retain generic text (e.g., such as patient age range, city, etc.) and synthetic anatomical features. These features may be used to group CT images and assess progression of coronary artery disease as a function of age and other related medical factors. Any suitable medical analysis may be performed using PHI-free data.

Server systems 10 and client systems 20 may be implemented by any conventional or other computer systems preferably equipped with a display or monitor, a base (including at least one hardware processor (e.g., microprocessor, controller, central processing unit (CPU), etc.), one or more memories and/or internal or external network interfaces or communications devices (e.g., modem, network cards, etc.), optional input devices (e.g., a keyboard, mouse or other input device), and any commercially available and custom software (e.g., server/communications software, machine learning and synthetic data generating system software, browser/interface software, etc.). By way of example, the server/client includes at least one processor 16, 22 one or more memories 17, 24 and/or internal or external network interfaces or communications devices 18, 26 such as a modem or network cards, and a user interface 19, 28 etc. The optional input devices may include a keyboard, mouse, or other input device.

Alternatively, one or more client systems 20 may perform identification and removal/replacement of PHI on or associated with medical images as a stand-alone device or unit. In a stand-alone mode of operation, the client system stores or has access to the data, such as PHI dataset 32, and generates synthetic dataset 36, and PHI-free dataset 38, and includes machine learning and synthetic data generating system 15. The graphical user or other interface 19, 28, such as a GUI, command line prompts, menu screens, etc., solicits information from a corresponding user pertaining to the desired identification and PHI mitigation, and may provide reports including analysis results. In some aspects, the PHI-free dataset may be analyzed to correlate medical diagnostic information with characteristics of the dataset.

Machine learning and synthetic data generating system 15 may include one or more modules or units to perform the various functions of present invention embodiments described herein. The various modules, such as text classifier 105, OCR and image-based classifier 110, deep-learning classifier 115, generative adversarial network 120, morphological network 122, and image synthesizer 130, etc., may be implemented by any combination of any quantity of software and/or hardware modules or units, and may reside within memory 17 of the server for execution by processor 16. These modules are described in additional detail below.

Figure 2:
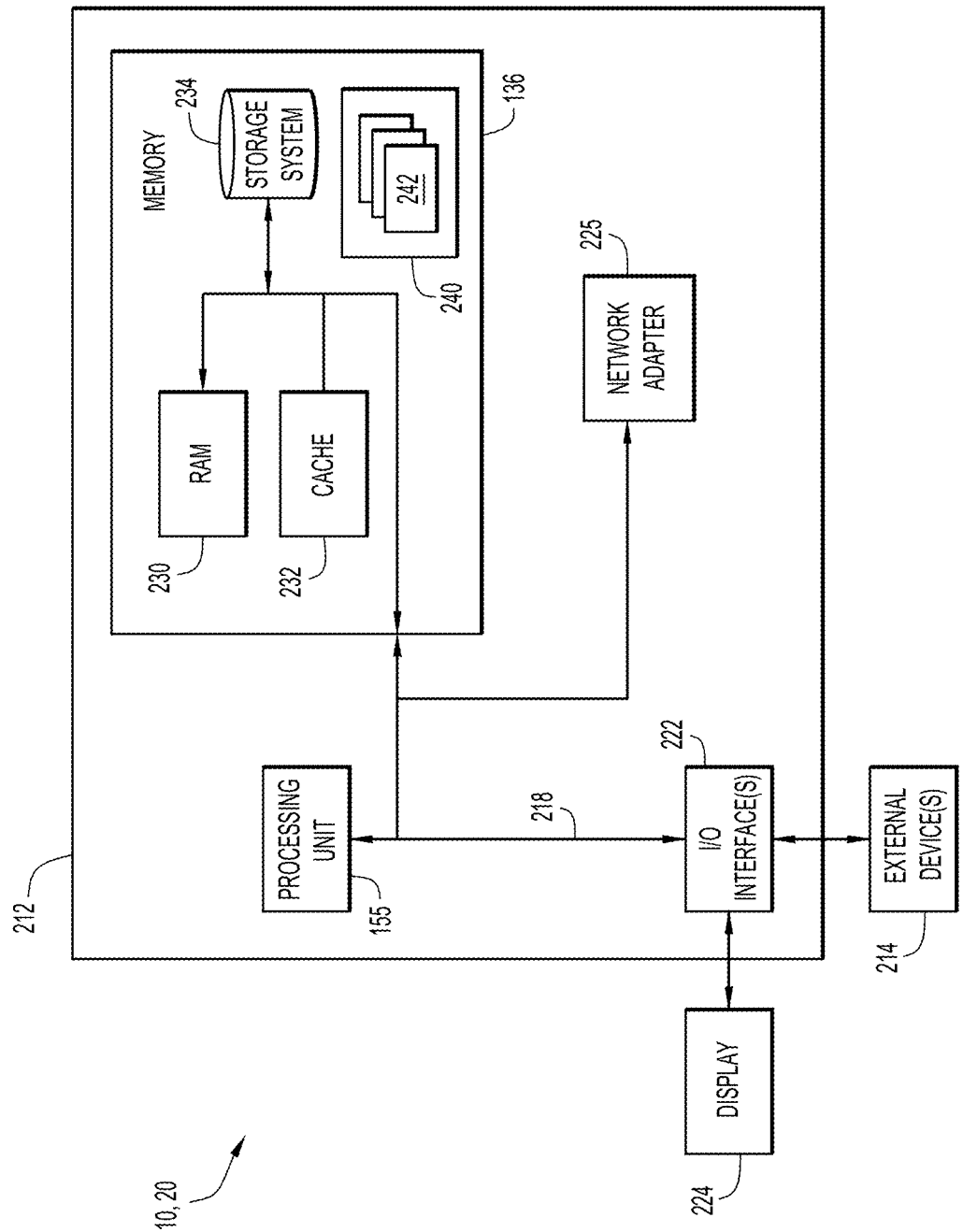
FIG. 2 is an example computing device for the computing environment of FIG. 1, according to an embodiment of the present invention.

Client systems 20 and server systems 10 may be implemented by any suitable computing device, such as the computing device 212 shown in FIG. 2 for computing environment 100. This example is not intended to suggest any limitation as to the scope of use or functionality of embodiments of the invention described herein. Regardless, computing device 212 is capable of being implemented and/or performing any of the functionality set forth herein.

In the computing device, there is a computer system which is operational with numerous other general purpose or special purpose computing system environments or configurations. Examples of well-known computing systems, environments, and/or configurations that may be suitable for use with the computer system include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 212 may be described in the general context of computer system executable instructions, such as program modules (e.g., machine learning and synthetic data generating system 15 and its corresponding modules), being executed by a computer system. Generally, program modules may include routines, programs, objects, components, logic, data structures, and so on that perform particular tasks or implement particular abstract data types.

Computer system 212 is shown in the form of a general-purpose computing device. The components of computer system 212 may include, but are not limited to, one or more processors or processing units 155, a system memory 136, and a bus 218 that couples various system components including system memory 136 to processor 155.

Bus 218 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 212 typically includes a variety of computer system readable media. Such media may be any available media that is accessible by computer system 212, and it includes both volatile and non-volatile media, removable and non-removable media.

System memory 136 can include computer system readable media in the form of volatile memory, such as random access memory (RAM) 230 and/or cache memory 232. Computer system 212 may further include other removable/non-removable, volatile/non-volatile computer system storage media. By way of example only, storage system 234 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 218 by one or more data media interfaces. As will be further depicted and described below, memory 136 may include at least one program product having a set (e.g., at least one) of program modules that are configured to carry out the functions of embodiments of the invention.

Program/utility 240, having a set (at least one) of program modules 242 (e.g., machine learning and synthetic data generating system 15 and corresponding modules, etc.) may be stored in memory 136 by way of example, and not limitation, as well as an operating system, one or more application programs, other program modules, and program data. Each of the operating system, one or more application programs, other program modules, and program data or some combination thereof, may include an implementation of a networking environment. Program modules 242 generally carry out the functions and/or methodologies of embodiments of the invention as described herein.

Computer system 212 may also communicate with one or more external devices 214 such as a keyboard, a pointing device, a display 224, etc.; one or more devices that enable a user to interact with computer system 212; and/or any devices (e.g., network card, modem, etc.) that enable computer system 212 to communicate with one or more other computing devices. Such communication can occur via Input/Output (I/O) interfaces 222. Still yet, computer system 212 can communicate with one or more networks such as a local area network (LAN), a general wide area network (WAN), and/or a public network (e.g., the Internet) via network adapter 225. As depicted, network adapter 225 communicates with the other components of computer system 212 via bus 218. It should be understood that although not shown, other hardware and/or software components could be used in conjunction with computer system 212. Examples, include, but are not limited to: microcode, device drivers, redundant processing units, external disk drive arrays, RAID systems, tape drives, and data archival storage systems, etc.

Figure 3:
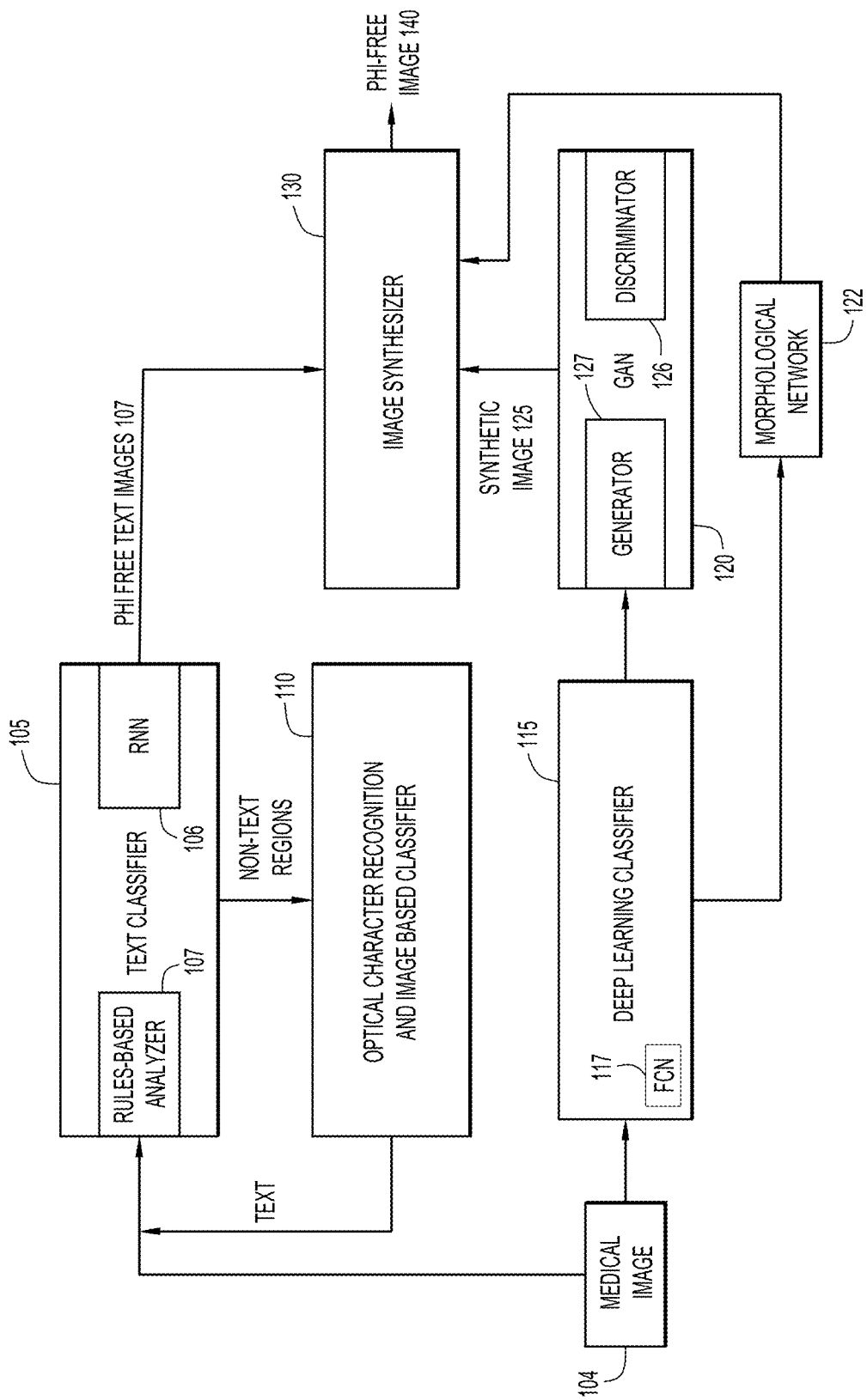
FIG. 3 is a flow diagram showing an example data flow between components of a machine learning and synthetic data generating system, according to an embodiment of the present invention.

FIG. 3 is a flow diagram showing the various modules and outputs of the machine learning and synthetic data generating system 15. Medical image 104 is provided to the text classifier 105 and to the deep learning classifier 115. Text classifier 105 may receive the medical images, which may be in a time-series format. Text classifier 105 may analyze the files for text-based information, e.g., text in the file header, file metadata, associated reports linked to the file, etc., that contains PHI. Analysis may be performed using a recursive neural network (RNN) 106 to identify PHI (e.g., text-based PHI) for time-series medical imaging studies.

Once the PHI is identified, a rules-based analyzer 107 may be used to replace identified PHI with generic PHI. Generic PHI contains characteristics of the patient-specific PHI but maintains patient privacy. Accordingly, the rules-based analyzer 107 aims to genericize PHI in a manner that reduces data loss while maintaining quality of the data to the extent that patient privacy is not compromised. In some cases, redaction may be performed by the rules-based analyzer, if a generic equivalent cannot be generated or does not protect patient privacy.

In some cases, headers of medical image files may contain private fields that contain PHI. The private field name/tag associated with the private field may not correlate with the content of the information contained in the private field. According to present approaches, the machine learning and synthetic data generating system 15 can analyze and classify information associated with private fields, independently of the name of the private field name/tag, to determine whether such fields contain PHI.

In some cases, the image may have embedded text present in the body of the digital image, such as burned in text (e.g., age, birthdate, name, etc.), generated by the image acquisition software. The image may be subjected to optical character recognition (OCR) by optical character recognition and image based classifier 110 to identify the embedded text to create a machine readable version of the embedded text. The resultant machine readable text may be provided to text classifier 105 for further analysis. In some cases, the embedded or burned in text may be redacted, while in other cases, the embedded text may undergo an image restoration or correction process, in which embedded text portions are filled in based on the digital image. The embedded text, if not present in the header file, may be added to the header file in a genericized manner. The genericized PHI along with the PHI containing image may be provided to the image synthesizer 130 for integration with the output of GAN 120.

The image may be provided to deep learning classifier 115 to identify features of the digital image that may contain private health identification. The deep learning classifier 115 may analyze the image on a pixel by pixel basis, and provide a probability associated with each pixel, regarding whether or not that pixel contains PHI. In some aspects, deep learning classifier 115 may use a fully convolutional network (FCN) 117 to perform pixel analysis.

Figure 4:
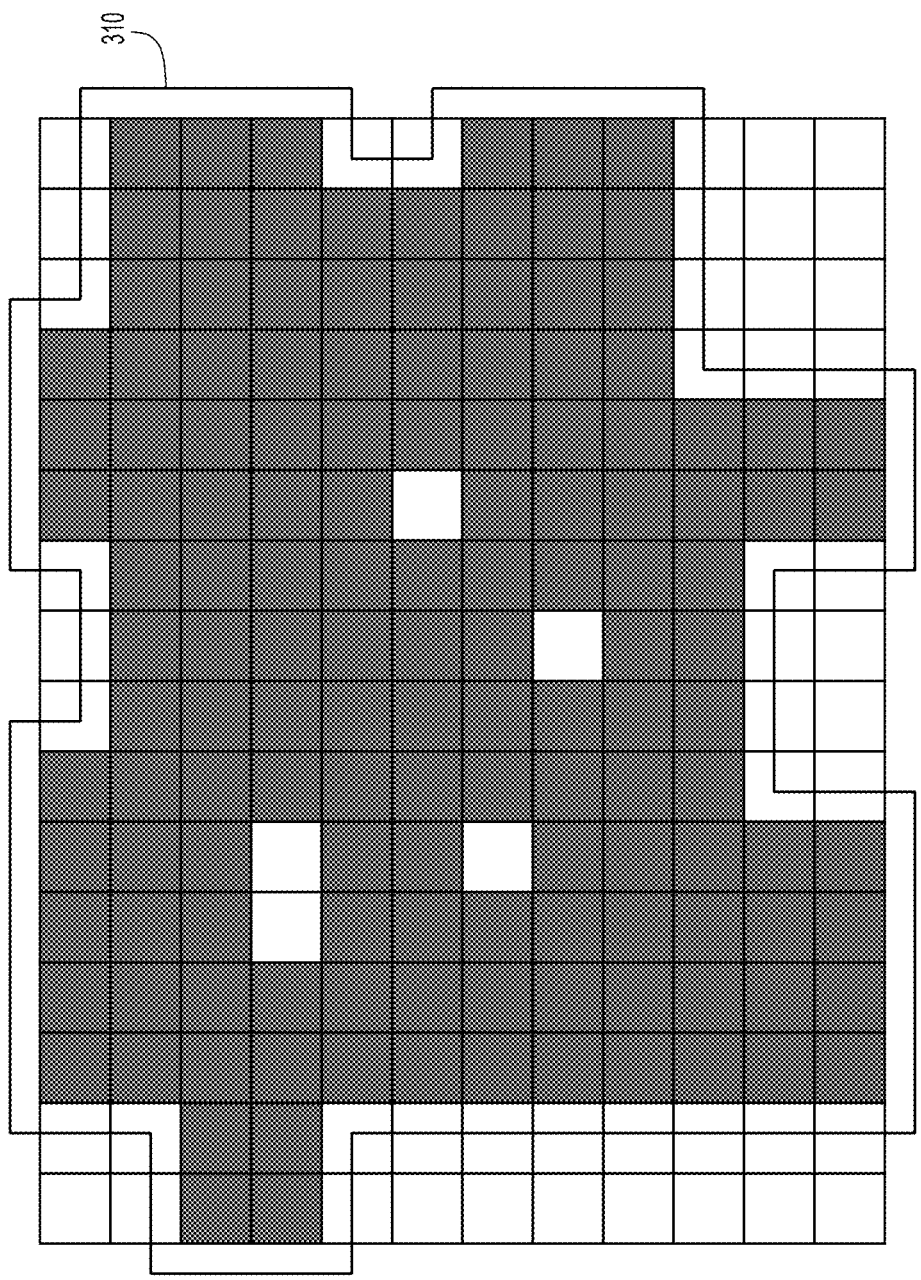
FIG. 4 is an example of generating bounded regions by the machine learning and synthetic data generating system, according to an embodiment of the present invention.

Once each pixel has an associated probability, the deep learning classifier 115 may establish boundaries 310 around groups of pixels in proximity to each other, as shown in FIG. 4. The shaded areas correspond to pixels having a probability (e.g., over a threshold value) associated with containing PHI. As shown in this figure, these pixels may be grouped together to form a region surrounded by a boundary 310, wherein the region may include a limited number of non-shaded pixels for continuity. This information (e.g., the bounded region containing PHI and the respective location of the bounded region relative to the digital image) may be provided to GAN 120, for synthetic image generation.

Referring back to FIG. 3, the deep learning classifier 115 may communicate with a GAN 120, to indicate which regions (e.g., bounded regions) contain PHI. GAN 120 may generate one or more synthetic images free of PHI to combine with the PHI-containing digital image.

For areas outside the region of interest that contain PHI, a GAN may generate synthetic GAN images 125 that have a realistic or natural appearance relative to the medical image 104. These images may be provided to image synthesizer 130, which may overlay the synthetic GAN images 125 onto the image with genericized text-PHI to produce a PHI-free image 140.

GANs typically comprise at least two neural networks. For example, GAN 120 may comprise a generator 127 that generates images and a discriminator 126 to classify the images as real or fake images. As training of the opposing neural networks progresses, the generator improves the quality of the computer generated images based on feedback from the discriminator. In the beginning of training, the GAN 120 may generate images that are not realistic (e.g., incorrect number of anatomical features, anatomical features in improper locations, loss of dimensionality or flat looking images, etc.). As training progresses, the GAN learns how to generate more realistic and natural images (e.g., features in proper locations, correct number of appendages, 3D appearance, etc.).

Image synthesizer 130, which receives PHI-free text image 107 (including the image without text-based PHI), may overlay PHI-free text image with the synthetic images 125 generated by the GAN that are free of PHI. Accordingly, the resultant PHI-free images 140 are free of both text-based PHI (associated with the header or burned into the file) and image PHI (e.g., identifying features, such as dental implants, facial features, body markings, metal implants, etc.), present in the medical image.

Image-based classifier 115 may identify regions containing both medically relevant information and PHI. Morphological network 122 may morph aspects of the digital image to conceal patient identification, while maintaining medically relevant information. For example, the system may keep the medically relevant portion, and morph other identifying features (e.g., eyes, nose, etc.) to prevent patient identification.

Thus, text classifier 105, OCR and image-based classifier 110, deep learning classifier 115, GAN 120, morphological network 122, and image synthesizer 130 are configured to operate in concert to automatically remove all identified PHI from medical imaging studies without manual human intervention. According to present embodiments, these operations may be used in an automated manner to replace all detectable PHI in an image of any modality.

In some aspects, the image may be CT images or MRI images. The images may be obtained as a time-series based set of images. Other image types, in addition to MRI and CT, that may be analyzed according to the techniques provided herein, include but are not limited to ultrasound, PET scan, X-ray, etc. Present techniques may be used for 2D or 3D images.

Figure 5:
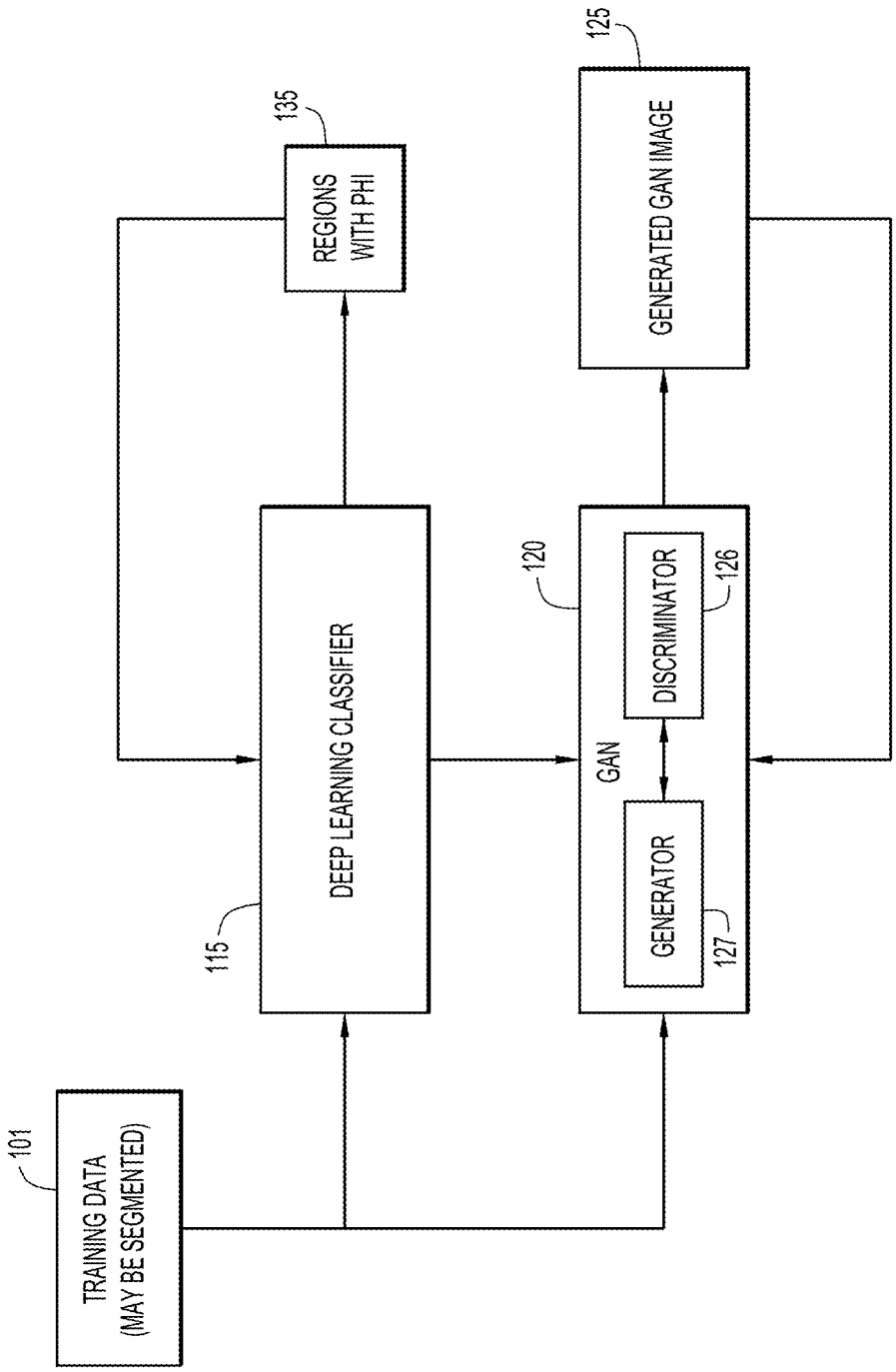
FIG. 5 is a flow diagram of example operations for training a deep learning classifier and a generative adversarial network to generate synthetic data, according to an embodiment of the present invention.

FIG. 5 shows aspects of training the deep learning classifier 115 and GAN 120. Training data 101, which may be segmented, may be provided to the deep learning classifier 115 and the GAN 120. By training the GAN with a type of image (e.g., a CT scan of the brain), the generator 127, which may be a neural network, will generate new images having similarity to the images provided in the training data. This new image may be provided to the discriminator 126, which will discern whether the new image is a real medical image (obtained from a patient) or a fake image (created by the generator 127). As training progresses, the discriminator 126 loses the ability to discern between real images and fake images, as the quality of the created images improve. Training may proceed until a threshold is passed (e.g., a certain percentage of fake images are classified as being real), and are therefore, of a suitable quality to incorporate into PHI free text images 107. In some aspects, generated GAN images 125, may be reviewed during training or at intervals during operation, to ensure image generation criteria (producing realistic images) are met.

Similarly, deep learning classifier 115 may undergo training to generate bounded regions to provide to the GAN. As training progresses, the classifier improves with discerning anatomic or other unique features that may be used for patient identification from medically relevant regions without PHI. Regions with PHI 135 may be reviewed and fed back to the system to ensure accuracy of pixel classification, and the deep learning classifier 115 may be retrained on this data as needed.

Figure 6:
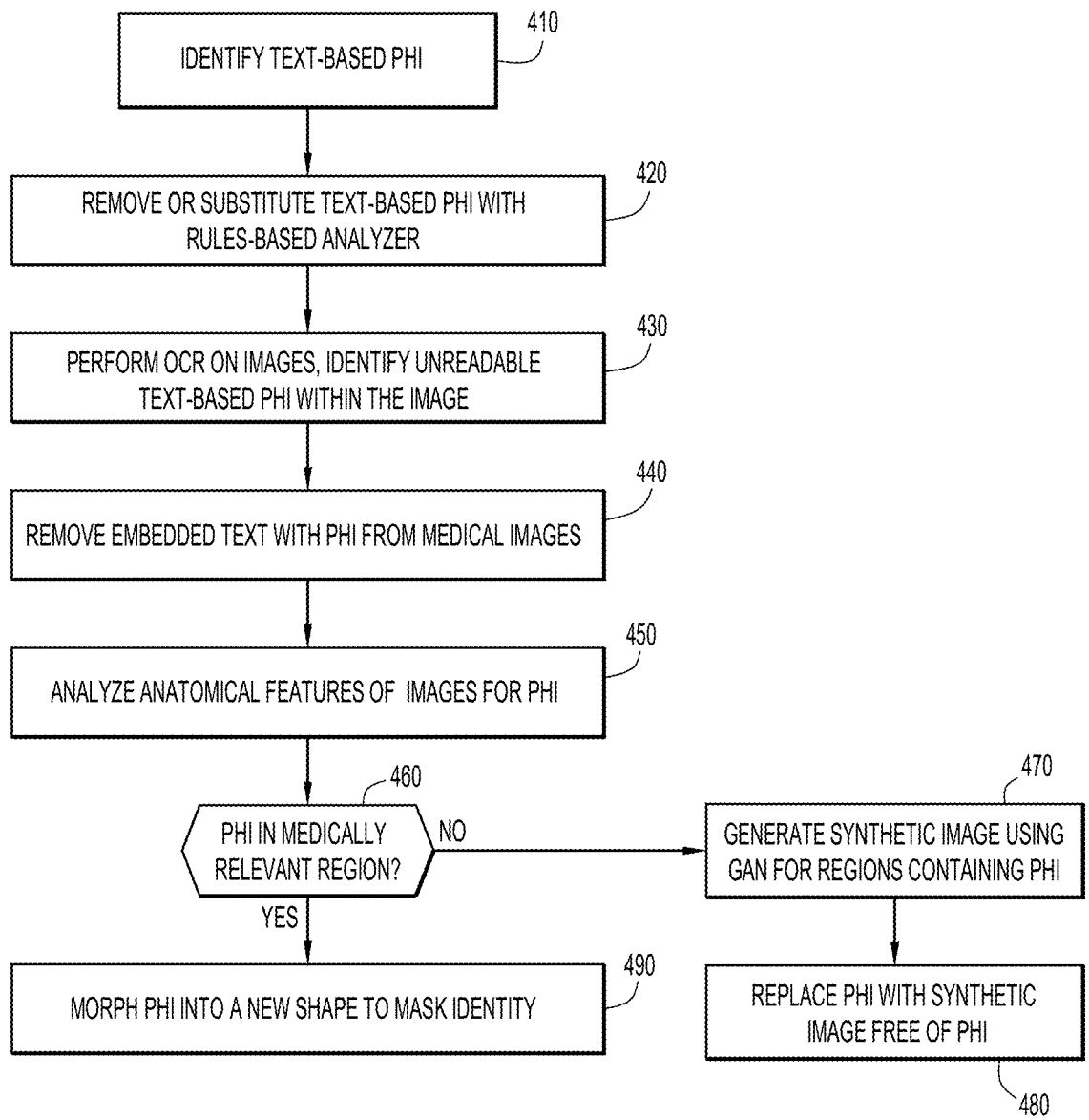
FIG. 6 is a detailed flowchart showing example operations for automatically removing PHI, according to an embodiment of the present invention.

FIG. 6 shows a flowchart of specific operations associated with the machine learning and synthetic data generating system 15. At operation 410, text-based PHI is identified. PHI may be present in header information associated with an image file, in metadata associated with an image file, or any other text-based information linked to or associated with the image file. In some aspects, the image may utilize a DICOM format, an XML-based format, a medical imaging network transport format, or any other suitable image-based format (e.g., JPEG, TIFF, GIF, PNG, etc.), or any other suitable equivalent.

For example, text classifier 105 may scan and analyze text-based information in DICOM image headers, associated DICOM structured reports, and any other medical report data associated or linked to the image.

In some aspects, the text classifier may utilize RNN 106 trained on DICOM headers that have been labeled to indicate phrases containing PHI. PHI may include, but is not limited to, patient name, patient identifier (e.g., numeric identifier), patient address, age, patient birthdate, type of medical imaging study, gender, weight, medical history, date of imaging study, equipment settings used to generate imaging study, medical facility and geographic data associated with the medical imaging study, etc. RNNs may be used to analyze time-series based information. Other types of machine learning algorithms may be employed to identify PHI in time-series based imaging studies, including long short-term memory (LSTMs) units, recurrent networks, or any other suitable type of neural network capable of identifying patterns in temporal sequences of data (e.g., text, etc.).

At operation 420, after RNN 106 has identified PHI, rules-based analyzer 107 may be used to genericize PHI. In some aspects, RNNs may be paired with one or more rules-based algorithms for replacing identified PHI containing fields with generic content. Thus, PHI may be modified so that patient identification cannot be performed, while characteristics of the PHI are retained (e.g., age range instead of age, city instead of address, etc.).

In some instances, if the DICOM images (or other images) are stored in a repository, the system 15 may analyze the characteristics of the stored data to determine whether to genericize the data. The system may track statistical information associated with data characteristics in order to identify specific PHI or combinations of PHI for generalization.

In some aspects, the system may consider characteristics of the text fields, and may generalize data stored in the text field or combinations of data thereof to preserve characteristics of the patient specific data while maintaining patient privacy. For example, if the dataset contains a single person of age 51 associated with an imaging study, the system may substitute the age of the individual in the DICOM with an age range encompassing a group of patients, to prevent identification based on age. However, if the dataset (PHI dataset 32) is analyzed and is determined to contain a large number of 51 year olds, age may not need to be genericized as the patient would not be able to be identified from age alone.

The system may also consider combinations of PHI to determine which fields to genericize. For example, the DICOM header may contain gender, age, and city of residence. While each parameter individually may not allow identification of the individual, the combined group may only have one member of a specific gender and age living in a specific city. Thus, the system may generalize PHI based upon combinations of categories.

At operation 430, OCR may be performed on the image to identify non-readable text and produce a machine rendered version of that text. OCR may be used to extract text from each image of the time series of images. The extracted text may be provided to the RNN of the text classifier 105, to identify text-based PHI.

At operation 440, the processed text is analyzed by the text classifier 105 to find and remove/modify text containing PHI. In some cases, the identified text may be redacted in the image and/or added to the DICOM header of the file. In other cases, if the identified text is duplicative of text present in the DICOM header, the duplicative data will not need to be retained, and may be redacted from the image. Alternatively, the image may undergo image correction to remove the embedded text.

At operation 450, the image itself may be analyzed to identify anatomical features that could be used to identify the patient. Deep learning classifier 115 may be used to analyze anatomical or other features of the image (e.g., each image in the time-series) that may identify the patient. For example, these features may include an individual's face, dental implants, medical implants, body markings, birthmarks, jewelry, abnormalities, or other unique features. Deep learning classifier 115 labels pixels as having a probability of containing PHI or not containing PHI to determine which pixels or regions thereof to provide to the GAN.

In other cases, PHI features may be reconstructed from multiple images (e.g., an image stack with respect to a vertical axis), such as reconstructing a face. Regions with PHI may be provided to GAN 120, and the GAN creates a corresponding image (fake image) without PHI to replace the portion of the image with PHI.

In some aspects, a fully convolutional network (FCN) may be trained on strongly labeled medical image series to identify which pixels/voxels in the time series contain anatomy or other features that could be used to identify the patient, e.g., if viewed with an appropriate 3D rendering tool. However, algorithms operating on regions (groups of pixels rather than individual pixels, would also be suitable, including general segmentation or detection algorithms with localization components).

At operation 460, the system determines whether the PHI containing region is pertinent to the medical study performed. The system determines whether removal of the PHI may unintentionally remove pertinent medical information.

If removal of the PHI would also remove medical information pertinent to the imaging study, the system proceeds to operation 490. Otherwise, if removal of the PHI has no discernable impact on the medical information of the imaging study, or if the region that includes PHI is separate from and non-overlapping with regions containing medical information pertinent to a diagnosis, the system proceeds according to operation 470.

At operation 470, GAN 120 may be used to generate synthetic images to be integrated into the medical imaging study, replacing identified features containing PHI, to preserve patient privacy. To generate synthetic images, GANs may be trained on the same data used to train deep learning classifier 115. In some cases, a GAN may be trained on entire body regions (e.g., the entire image). In other cases, GANs may be trained for each body region for which a synthetic image is to be generated. For example, in some aspects, the body may be segmented into head, neck, shoulders, chest, abdomen, pelvis, legs, hand, foot, and arm regions. For each body region, the GAN may be trained to generate generic body parts to replace image content that identifies the patient. For example, the GAN may be trained to generate a realistic face if the deep learning classifier 115 determines that the face is visible in the images (and not medically relevant). The synthetic images generated by GAN 120 retain a realistic appearance without identifying the patient.

Additionally, by generating realistic replacement images and overlaying (replacing) these images onto the corresponding portion of the medical image according to operation 480 (instead of generating redacted images with the face or other features cropped out), the images may continue to be used in applications that rely on image registration and multi-atlas segmentation, which may be unable to correctly process images with missing or redacted regions. For example, some applications rely on the presence of certain features, e.g., the face or skull, when processing images. Removing these features by redaction may result in incorrect output by the application or the inability of the application to load and process the image. Present techniques preserve image content, by replacing or modifying regions containing PHI, allowing such applications to function properly.

As previously discussed, the image-based classifier 115 may identify regions containing medical information and PHI. At operation 490, morphological network 122 may alter other structures to preserve identity. For example, a facial structure (e.g., shape of face, eyes, noses, etc.) may be morphed into a different face, changing the overall shape of the face to prevent patient identification, while maintaining medically relevant information that may comprise PHI.

Figure 7:
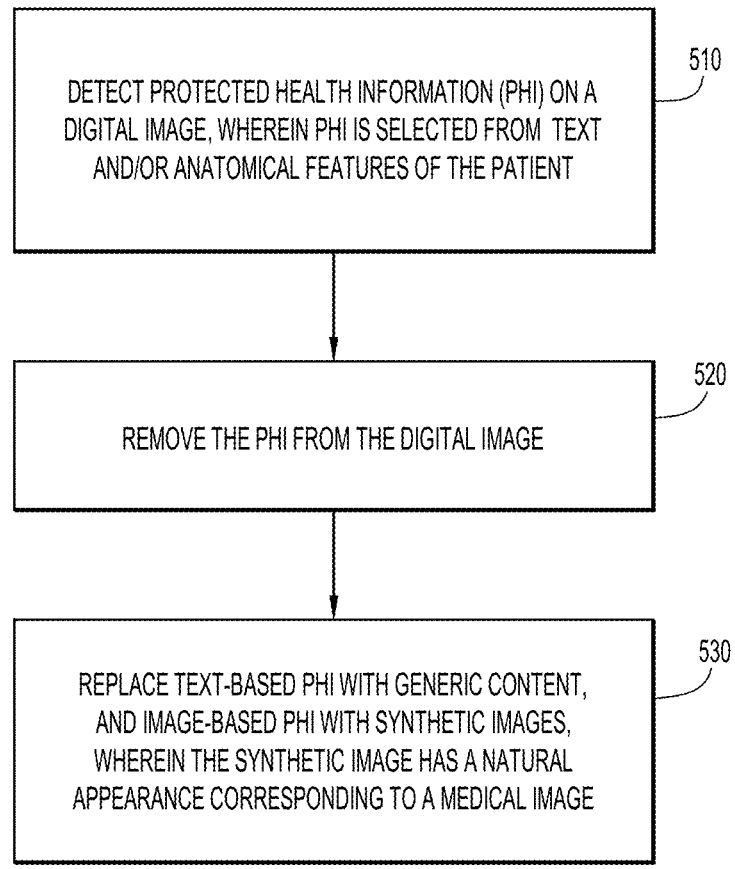
FIG. 7 is a high level flowchart of example operations for automatically removing PHI, according to an embodiment of the present invention.

FIG. 7 shows example high level operations of using a synthetic data and generative machine learning system 15 to manage PHI or other identifying information by identifying and mitigating PHI. At operation 510, the synthetic data and generative machine learning system detects protected health information embedded in a digital image, wherein PHI is selected from text and anatomical features of the patient. At operation 520, PHI is removed from the digital image. At operation 530, text-based PHI is replaced with generic content, and image-based PHI is replaced with synthetic images, wherein the synthetic image has a natural appearance as compared to the digital image. PHI-free images may be generated by a generative adversarial network. Text-free PHI may be generated by a rules-based platform.

The present system automatically removes PHI or other identifying information using a plurality of approaches. Compared to existing PHI removal systems, the present techniques replace sensitive text and image content with generic or synthetic content, rather than simply redacting the identified PHI. This approach minimizes data loss, retains the natural appearance of the data and bulk characteristics, while promoting quality and sharing of the PHI-free digital images with various processing applications.

It will be appreciated that the embodiments described above and illustrated in the drawings represent only a few of the many ways of implementing embodiments for automating identification and mitigation of PHI by replacing PHI-containing content with more generalized content and/or modified or morphed images.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, machine learning and synthetic data generating system 15, etc.). These systems may include any type of monitors and input devices (e.g., keyboard, mouse, voice recognition, etc.) to enter and/or view information.

It is to be understood that the software (e.g., machine learning and synthetic data generating system 15, including text classifier 105, OCR and image-based classifier 110, deep learning classifier 115, generative adversarial network 120, morphological network 122, image synthesizer 130, etc.) of the present invention embodiments may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

The software of the present invention embodiments (e.g., machine learning and synthetic data generating system 15, including text classifier 105, OCR and image-based classifier 110, deep learning classifier 115, generative adversarial network 120, morphological network 122, image synthesizer 130, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., machine learning and synthetic data generating system 15, including text classifier 105, OCR and image-based classifier 110, deep learning classifier 115, generative adversarial network 120, morphological network 122, image synthesizer 130, etc.). The database system may be implemented by any number of any conventional or other databases, data stores or storage structures (e.g., files, databases, data structures, data or other repositories, etc.) to store information (e.g., PHI dataset 32, synthetic dataset 36, PHI-free dataset 36, etc.). The database system may be included within or coupled to the server and/or client systems. The database systems and/or storage structures may be remote from or local to the computer or other processing systems, and may store any desired data (e.g., PHI dataset 32, synthetic dataset 36, PHI-free dataset 36, etc.).

The present invention embodiments may employ any number of any type of user interface (e.g., Graphical User Interface (GUI), command-line, prompt, etc.) for obtaining or providing information (e.g., PHI dataset 32, synthetic dataset 36, PHI-free dataset 36, etc.), where the interface may include any information arranged in any fashion. The interface may include any number of any types of input or actuation mechanisms (e.g., buttons, icons, fields, boxes, links, etc.) disposed at any location to enter/display information and initiate desired actions via any suitable input devices (e.g., mouse, keyboard, etc.). The interface screens may include any suitable actuators (e.g., links, tabs, etc.) to navigate between the screens in any fashion.

The output of the machine learning and synthetic data generating system 15 may include any information arranged in any fashion, and may be configurable based on rules or other criteria to provide desired information to a user (e.g., classification results, image analysis results, PHI analytics, medical analysis based on the PHI images and PHI-free images, etc.).

The present invention embodiments are not limited to the specific tasks or algorithms described above, but may be utilized for any application in which removal of PHI is useful. For example, while the present examples are in the context of neural networks, any suitable classifier may be used. Further, this approach may be generally applicable to mitigate any identifying or other information in any context, and is not limited to medical implementations.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method, in a data processing system comprising at least one processor and at least one memory, the at least one memory comprising instructions executed by the at least one processor to cause the at least one processor to manage identifying information for an entity, the method comprising:
    detecting the identifying information of the entity associated with a digital image, wherein the identifying information includes text information identifying the entity and image information corresponding to one or more anatomical features identifying the entity;
    removing the text information from the digital image; and
    replacing the image information with one or more computer generated synthetic images of the one or more anatomical features, wherein the computer generated synthetic images are based on a natural appearance of the one or more anatomical features in the digital image.

2. The method of claim 1, further comprising:
    classifying each pixel of the digital image using a deep learning classifier with respect to containing the identifying information;
    generating regions corresponding to groups of pixels containing the identifying information; and
    replacing the regions that contain the identifying information with synthetic images generated by a generative adversarial network (GAN).

3. The method of claim 2, wherein the entity is a patient and the classifying further comprises:
    determining that a region containing the identifying information is relevant to a medical diagnosis; and
    morphing the image information to alter anatomical features of the patient that are not in the relevant region.

4. The method of claim 2, further comprising:
    generating a candidate synthetic image by a discriminator neural network;
    determining by an adversarial neural network whether the candidate synthetic image is real or computer-generated;
    iteratively regenerating the candidate synthetic image, until the adversarial neural network determines that the candidate synthetic image is real; and
    when the adversarial neural network determines that the candidate synthetic image is real, replacing corresponding image information with the candidate synthetic image.

5. The method of claim 2, wherein the deep learning classifier comprises a fully convolutional network (FCN).

6. The method of claim 2, wherein the entity includes a patient and the method further comprising:
    segmenting the digital image into different portions corresponding to particular anatomical features of the patient; and
    classifying each pixel of the portions using the deep learning classifier with respect to containing the identifying information.

7. The method of claim 1, further comprising:
    identifying a header associated with the digital image that contains private fields and text;
    analyzing the private fields and text using a recursive neural network (RNN) for the text information; and
    replacing the text information in the private fields and header with generic text comprising characteristics of the text information while maintaining entity privacy.

8. The method of claim 1, further comprising:
    performing OCR on the digital image to identify text embedded in the digital image;
    generating machine readable text from the embedded text and evaluating the machine readable text for the identifying information; and
    removing portions of the embedded text from the digital image that contains the identifying information.

9. An apparatus for managing identifying information for an entity, the apparatus comprising:
    one or more processors;
    one or more computer readable storage media;
    program instructions stored on the one or more computer readable storage media for execution by at least one of the one or more computer processors, the program instructions comprising instructions to:
        detect the identifying information of the entity associated with a digital image, wherein the identifying information includes text information identifying the entity and image information corresponding to one or more anatomical features identifying the entity;

remove the text information from the digital image; and replace the image information with one or more computer generated synthetic images of the one or more anatomical features, wherein the computer generated synthetic images are based on a natural appearance of the one or more anatomical features in the digital image.

10. The apparatus of claim 9, wherein the program instructions further comprise instructions to:

classify each pixel of the digital image using a deep learning classifier with respect to containing the identifying information;

generate regions corresponding to groups of pixels containing the identifying information; and replace the regions that contain the identifying information with synthetic images generated by a generative adversarial network (GAN).

11. The apparatus of claim 10, wherein the entity is a patient and the program instructions further comprise instructions to:

determine that a region containing the identifying information is relevant to a medical diagnosis; and morph the image information to alter anatomical features of the patient that are not in the relevant region.

12. The apparatus of claim 10, wherein the program instructions further comprise instructions to:

generate a candidate synthetic image by a discriminator neural network;

determine by an adversarial neural network whether the candidate synthetic image is real or computer-generated;

iteratively regenerate the candidate synthetic image, until the adversarial neural network determines that the candidate synthetic image is real; and when the adversarial neural network determines that the candidate synthetic image is real, replace corresponding image information with the candidate synthetic image.

13. The apparatus of claim 10, wherein the entity is a patient and the program instructions further comprise instructions to:

segment the digital image into different portions corresponding to particular anatomical features of the patient; and classify each pixel of the portions using the deep learning classifier with respect to containing the identifying information.

14. The apparatus of claim 9, wherein the program instructions further comprise instructions to:

identify a header associated with the digital image that contains private fields and text;

analyze the private fields and text using a recursive neural network (RNN) for the text information; and replace the text information in the private fields and header with generic text comprising characteristics of the text information while maintaining entity privacy.

15. The apparatus of claim 9, wherein the program instructions further comprise instructions to:

perform OCR on the digital image to identify text embedded in the digital image;

generate machine readable text from the embedded text and evaluate the machine readable text for the identifying information; and remove portions of the embedded text from the digital image that contains the identifying information.

16. A computer program product for configuring processing elements within a distributed computing system, the computer program product comprising one or more computer readable storage media collectively having program instructions embodied therewith, the program instructions executable by a computer to cause the computer to:

detect the identifying information of the entity associated with a digital image, wherein the identifying information includes text information identifying the entity and image information corresponding to one or more anatomical features identifying the entity;

remove the text information from the digital image; and replace the image information with one or more computer generated synthetic images of the one or more anatomical features, wherein the computer generated synthetic images are based on a natural appearance of the one or more anatomical features in the digital image.

17. The computer program product of claim 16, wherein the program instructions further cause the computer to:

classify each pixel of the digital image using a deep learning classifier with respect to containing the identifying information;

generate regions corresponding to groups of pixels containing the identifying information; and replace the regions that contain the identifying information with synthetic images generated by a generative adversarial network (GAN).

18. The computer program product of claim 17, wherein the program instructions further cause the computer to:

generate a candidate synthetic image by a discriminator neural network;

determine by an adversarial neural network whether the candidate synthetic image is real or computer-generated;

iteratively regenerate the candidate synthetic image, until the adversarial neural network determines that the candidate synthetic image is real; and when the adversarial neural network determines that the candidate synthetic image is real, replace corresponding image information with the candidate synthetic image.

19. The computer program product of claim 16, wherein the program instructions further cause the computer to:

identify a header associated with the digital image that contains private fields and text;

analyze the private fields and text using a recursive neural network (RNN) for the text information; and replace the text information in the private fields and header with generic text comprising characteristics of the text information while maintaining entity privacy.

20. The computer program product of claim 16, wherein the program instructions further cause the computer to:

perform OCR on the digital image to identify text embedded in the digital image;

generate machine readable text from the embedded text and evaluate the machine readable text for the identifying information; and remove portions of the embedded text from the digital image that contains the identifying information.

* * * * *